United States Patent
He

(10) Patent No.: US 10,844,355 B2
(45) Date of Patent: *Nov. 24, 2020

(54) METHOD OF MEASURING INHIBITION OF PHOSPHATIDYLCHOLINE EXPORT TRANSPORT AND/OR FORMATION ACTIVITY

(71) Applicant: Biotranex, LLC, Monmouth Junction, NJ (US)

(72) Inventor: Kan He, Princeton, NJ (US)

(73) Assignee: Princeton Bioinnovation LLC, Monmouth Junction, NJ (US)

( * ) Notice: Subject to any disclaimer, the term of this patent is extended or adjusted under 35 U.S.C. 154(b) by 26 days.

This patent is subject to a terminal disclaimer.

(21) Appl. No.: 16/291,831

(22) Filed: Mar. 4, 2019

(65) Prior Publication Data
US 2019/0203172 A1    Jul. 4, 2019

Related U.S. Application Data

(63) Continuation of application No. 15/507,523, filed as application No. PCT/US2016/024778 on Mar. 29, 2016, now Pat. No. 10,280,401.

(60) Provisional application No. 62/148,296, filed on Apr. 16, 2015.

(51) Int. Cl.
*C12N 5/071*    (2010.01)
*G01N 33/50*    (2006.01)
*G01N 33/92*    (2006.01)
*C12N 5/00*     (2006.01)

(52) U.S. Cl.
CPC ......... *C12N 5/067* (2013.01); *G01N 33/5067* (2013.01); *G01N 33/92* (2013.01); *C12N 5/00* (2013.01); *G01N 2333/705* (2013.01)

(58) Field of Classification Search
CPC .................................................... C12N 5/067
See application file for complete search history.

(56) References Cited

PUBLICATIONS

Delong et al., JBC, 2002, 277(19):17217-17255.*
Morita et al., BioMed Research International, 2014, pp. 1-11.*

* cited by examiner

*Primary Examiner* — Bin Shen
(74) *Attorney, Agent, or Firm* — Thomas F. Woolf

(57) ABSTRACT

A method is provided to measure modulation of phosphatidylcholine export transport and/or formation activity in hepatocyte or stable cell-line preparations by test agents including but not limited to drugs, drug candidates, biologicals, food components, herb or plant components, proteins, peptides, DNA, and RNA. Furthermore, the method is designed to determine modulation of phosphatidylcholine transport and/or formation activity not only by said test agents, but also their metabolites or biotransformed products formed in situ.

23 Claims, 5 Drawing Sheets

R1 = saturated or unsaturated C16-C22 fatty acid
R2 = saturated or unsaturated C16-C22 fatty acid

METHOD OF MEASURING INHIBITION OF PHOSPHATIDYLCHOLINE EXPORT TRANSPORT AND/OR FORMATION ACTIVITY

CROSS REFERENCE TO RELATED APPLICATIONS

This application is a continuation of U.S. National Stage application number 15/507,523 filed on Feb. 28, 2017 under 35 U.S.C. § 371 of PCT/US2016/024778, filed on Mar. 29, 2016, which claims priority from U.S. Provisional application No. 62/148,296, filed on Apr. 16, 2015.

BACKGROUND OF THE INVENTION

Field of the Invention

The invention relates to the field of biological transporter proteins and modulation of these proteins. This invention relates to a novel method to detect and measure the interaction of a test agent with mammalian phosphatidylcholine (PC) export transport and/or formation activity.

Description of Related Art

P-glycoproteins (P-gp) are 170-kDa glycosylated membrane proteins that actively transport and export a wide range of substrates out of cells (Smith, A., et al.

MDR3 P-glycoprotein, a phosphatidylcholine translocase, transports several cytotoxic drugs and directly interacts with drugs as judged by interference with nucleotide trapping. J Biol Chem, 275[31], 23530-23539 p23531.). Two P-gp genes have been identified in humans that encode for the multidrug-resistant 1 and 3 P-glycoproteins (MDR1 and MDR3). Multidrug-resistant 3 P-glycoprotein is also referred to as multidrug resistance protein 3 and is used interchangeably, MDR1 and MDR3 are members of the ATP-binding cassette (ABC) transporter family and are also named ATP-binding cassette proteins B1 (ABCB1) and B4 (ABCB4), respectively (Smith, id., p23531.; Yoshikado, T., et al. [2011]. Itraconazole-induced cholestasis: involvement of the inhibition of bile canalicular phospholipid translocator MDR3/ABCB4. Mol Pharmacol, 79(2). 241-250. p 241; Zhao, Y., et al [2015]. ABCB4 exports phosphatidylcholine in a sphingomyelin-dependent manner. J Lipid Res. doi: 10.1194/jlr.M056622. p3.). MDR1 is associated with the export of several drugs and is involved in the resistance that cancer cells display to several anticancer agents (Smith, p23531.; Yoshikado, id., p241.). Based on the process by which MDR3 translocates PC from the inner to outer leaflet of cellular membranes, MDR3 is also described as a type of floppase protein and is involved in maintaining cannicular membrane integrity (Groep, A., et al. [2011]. Complementary functions of the flippase ATP8B1 and the floppase ABCB4 in maintaining canalicular membrane integrity. Gastroenterology, 141(5), 1927-1937. p1927.). MDR3 appears to play a lesser role in drug transport compared with MORI, although more examples continue to be found (Smith, id., p23531.).

MDR3 (ABCB4) is a 1279 amino acid protein that is divided into two homologous halves, each of which contains six transmembrane helices (TMHs) and a cytoplasmic nucleotide-binding fold (NBF) (Morita, S. Y., & Terada, T. [2014]. Molecular mechanisms for biliary phospholipid and drug efflux mediated by ABCB4 and bile salts. Biomed Res Int, 2014:954781. doi 10.1155/2014/954731. p1.). MDR1 is found in various tissues, including the aver, kidney, intestinal mucosa, and capillary endothelial cells at the blood-brain barrier, while MDR3 is expressed mainly in hepatic tissue, although low levels of MDR3 mRNA can be found in the adrenal gland muscle, tonsil, spleen, placenta, testis, and ileum (Morita & Terada, id., p1.).

Bile formation is one of the most essential functions of the liver, and several ATP-binding cassette (ABC) transporters are known to be involved in the biliary secretion of biliary lipids, organic solutes, and xenobiotics (Yoshikado, id., p 241.). Biliary secretion of bile salts and phos phospholipids, essential components of biliary micelles, are mediated by the bile salt export pump (BSEP also known as ABCB11) and by MDR3 respectively, and their genetic dysfunction can lead to severe cholestatic diseases (Yoshikado, id., p241.), Dysfunction of MDR3 results in a lack of phospholipids and a surplus of bile salts in primary bile, and this compositional imbalance causes damage to biliary canaliculi, leading to chronic and progressive liver diseases such as intrahepatic cholestasis and low phospholipid-associated cholelithiasis (LPAC) syndrome (Zhao, id., p3.).

In Abcb4 knockout mice models, biliary secretion of phospholipids is negligible and excretion of cholesterol is reduced (Morita & Terada, id., p3.). In Abcb4 heterozygous mice the secretion rate of phospholipids is reduced by about 30 to 50 percent, while cholesterol secretion remains similar to that found in wild-type mice (Morita & Terada, id., p3.). Mixed micelles of bile salts and phospholipids have a much higher capacity to take up cholesterol than simple bile salt micelles (Morita & Terada, id., p3.). In a vesicle model prepared from a yeast mutant expressing the mouse Abcb4 gene, the addition of the bile salt taurocholate increases the ABCB4 transporter activity for phospholipid (Morita & Terada id., p6.). The phospholipid efflux mediated by ABCB4 is increased with increasing concentrations of taurocholate and shows concentration dependence from 0.2 mM to 1 mM taurocholate (Morita & Terada, id., p6).

Mutations in the human MDR3 (ABCB4) gene are associated with a wide spectrum of hepatic injury phenotypes, ranging from progressive familial intrahepatic cholestasis type 3 (PFIC3) to adult cholestatic liver disorders (Morita & Terada, id., p3.). PFIC3 is characterized by high γ-glutamyl transpeptidase and early onset of persistent cholestasis that progresses to cirrhosis and liver failure before adulthood (Morita & Terada, id., p3.). In many cases of PFIC3, liver transplantation is the only therapy. The biliary phospholipid level in a PFIC3 patient is dramatically decreased despite the presence of bile salts (Morita & Terada, id., p3.).

Defects in the MDR3 transporter are associated with intrahepatic cholestasis of pregnancy (ICP), LPAC, and primary biliary cirrhosis (Morita & Terada id., p3.). ICP is a reversible form of cholestasis in the third trimester of pregnancy and is rapidly ameliorated after childbirth. LPAC is characterized by intrahepatic hyperechoic foci, intrahepatic sludge, or microlithiasis (Morita & Terada, id., p3.). The absence of biliary phospholipids may lead to the destabilization of micelles and promote the lithogenicity of bile with the crystallization of cholesterol (Morita & Terada, id., p3.), The association between cholangocarcinoma, a rare malignant tumor of the biliary tract, and ABCB4 mutations has recently been reported (Morita & Terada, id., p3.). Chronic biliary inflammation may increase cholangiocyte turnover, leading to the growth of altered cholangiocytes and increased susceptibility to cholangiocarcinoma (Morita & Terada, id., p3).

Hepatocytes: Hepatic parenchymal cells, or hepatocytes, are polyhedral or spherical in nature and account for approximately 60% of the cells in the liver; they represent 80% or more of the total liver volume (de la Iglesia, F. [1999]. Morphofunctional aspects of hepatic structure. In: Handbook of Drug Metabolism, Woolf, T. F., editor, New York: Dekke p83.). Hepatocytes are polar in nature, and one skilled in the art would recognize what is termed an apical (canalicular) membrane domain and a basolateral (blood or sinusoidal domain) membrane or domain. The hepatocyte basolateral membrane or domain is involved in the uptake of drugs and xenobiotics into the cell, while the apical membrane or domain provides a route for intracellular produced bile salts to be excreted or transported into bile flow and eventually to the common bile duct for secretion into the intestine.

Hepatocytes have specialized transport systems or transcellular transporters located at the basolateral membrane and the apical membrane (Morgan, R. E., et al. [2010]. Interference with bile salt export pump function is a susceptibility factor for human liver injury in drug development. Toxicol Sci, 118(2), 485-500. p485.). These hepatobiliary transporters maintain liver homeostasis by regulating intracellular exposure to endobiotic and xenobiotic chemicals. Transport systems comprising specific transporter proteins have been extensively investigated. Transporters at the basolateral membrane are involved in hepatocellular uptake of various substrates from the blood and sinusoids, elimination to the blood and sinusoids, or both depending on the transporter. Transporters on the apical membrane however, are exclusively efflux transporters, mediating secretion of various substrates into the bile flow including bile acids, phospholipids, and salts (Morgan, id., p485.).

Drug-Induced Liver Injury (DILI): Drug-induced liver injury encompasses a spectrum of clinical disease ranging from mild biochemical abnormalities to acute liver failure (Hussaini, S. H. & Farrington, E. A. [2007]. Idiosyncratic drug-induced liver injury: an overview. Expert Opin Drug Saf, 6(6), 673-684. Abstract.). Most frequently, the underlying mechanism of DILI is poorly understood. In some cases of DILI, the liver injury is categorized as idiosyncratic-unknown etiology (Lee, W. M. [2003]. Drug-induced hepatotoxicity. N Engl J Med, 349(5), 474-485. Abstract; Wolf, K. K. et al. [2010]. Use of cassette dosing in sandwich-cultured rat and human hepatocytes to identify drugs that inhibit bile acid transport. Toxicol In Vitro, 24(1), 297-309. p2.). The incidence of DILI-induced hepatotoxicity in clinically marketed drugs is relatively rare, ranging from 1 in 5,000 to 1 in 10,000 or less; particularly infrequently does DILI result in severe liver injury leading to irreversible liver failure that can be fatal or require liver transplantation. Despite this low incidence, DILI is a major cause of removal of approved drugs from the United States market resulting in removal of clinically significant therapeutics from patients in need of such therapy (Wolf, id., p1.; U.S. Department of Health and Human Services, Food and Drug Administration (FDA), Center for Drug Evaluation and Research, Center for Biologics Evaluation and Research. Guidance for Industry: Drug-induced liver injury—premarketing clinical evaluation. Silver Springs, Md.: FDA, July 2009, p1, Introduction.). Further consequences of DILI include class action lawsuits against the innovator company (with multimillion dollar settlements), and the addition of time, expense, and uncertainty to the drug discovery and development process.

The incidence of DILI in approved drugs is rare because modern drug development requires extensive preclinical testing of drug candidates and subsequent clinical trials. Drug candidates that display toxic potential are usually removed from development and never reach the market (FDA, id.). Nevertheless, some drugs that reach the market do produce DILI. Reasons for this may involve the relatively infrequent occurrence or nature of an adverse event and the fact that clinical trials are conducted in a closely controlled patient environment with a limited number of subjects for a limited time. Following marketing approval, the number of individuals who are administered a therapeutic agent will be much greater, periods of treatment may be much longer, and patients are less well monitored. Individuals display a wide variability in hepatic function and can differ greatly with respect to inherent hepatic metabolic function, environmental factors, and use of other medications. Risk factors for DILI include age, sex, and genetic polymorphisms of drug-metabolizing enzymes such as cytochrome P450. In patients with human immunodeficiency virus, the presence of chronic viral hepatitis increases the risk of antiretroviral therapy hepatotoxicity (Wolf, id.; Hussaini, id. Abstract.).

The relatively low incidence rate of DILI creates difficulties in detecting and diagnosing it, both in, lack of tests and in numbers of patients needed to be tested. There is no clinical finding that indicates the, presence of DILI with certainty, including liver biopsy. Because DILI may simulate a variety of known liver diseases, the histopathologic picture frequently is reported to be "compatible with" the clinical and laboratory information available, but is often not diagnostic. In fact, the diagnosis of DILI is one of exclusion, in which sufficient clinical information must be gathered to rule out other possible causes of abnormal findings. This kind of diagnosis requires collecting considerable data at the time of the acute clinical situation, a process that is frequently inefficiently and haphazardly done, and therefore available information is often inadequate to establish the likelihood of drug causality with a reasonable degree of confidence (FDA, id., pps3-7.).

In most controlled clinical trials, monitoring is done to detect hepatic injury by serum enzyme (typically aminotransferase) activity increase. Because risks associated with a new drug are unknown, caution dictates that stopping rules be used to limit liver damage during a trial. For safety reasons, the drug may be stopped before the full implication of its possible toxicity an be determined. Extrapolation of such potentially incomplete data is therefore often used to predict the likelihood of future severe toxicity of the drug in clinical use.

In order to interpret data from patients exposed to drugs in clinical trials, a hierarchy of findings that indicate progressively severe liver injury is used, beginning with Berm amino-transferase activity as the most frequently abnormal and most sensitive test (FDA, id.). In clinical trials of new drugs, 15% or more of study patients may demonstrate mild elevations of alanine aminotransferase (ALT) or aspartate aminotransferase (AST) activity. The threshold required to consider either more frequent monitoring of blood levels or stopping the drug is variously placed at twice the upper limit of the normal (ULN) or reference range (2×ULN), at 3×ULN, or at 5×ULN. Monitoring is typically performed on a monthly basis but may be increased to biweekly or weekly checking if elevations in serum enzyme levels are noted According to the FDA Guidance on Drug-Induced Diver Injury:

| Discontinuation of Treatment Should Be Considered When: |
| --- |
| ALT or AST > 8xULN |
| ALT or AST > 5xULN for more than 2 weeks |
| ALT or AST > 3xULN and (TBL > 2xULN or INR > 1.5) |
| ALT or AST > 3xULN with the appearance of fatigue, nausea, vomiting, right upper quadrant pain or tenderness, fever, rash, and/or eosinophilia (>5%) |

ALT—Alanine aminotransferase; AST—Aspartate aminotransferase; TBL—Total bilirubin levels; INR—Increased plasma thrombin time.
U.S. Department of Health and Human Services, Food and Drug Administration (FDA), Center for Drug Evaluation and Research, Center for Biologics Evaluation and Research. Guidance for Industry: Drug-induced liver injury - premarketing clinical evaluation. Silver Springs, MD: FDA, July 2009. Page 10.

Levels of 10xULN typically mandate immediate cessation of a drug or agent and are considered serious signals, but still do not represent true tests of liver function. Yet great difficulties persist in accurately determining, when abnormalities are seen, whether they are caused by DILI or by some other disorder (FDA, id., pps3-7, 10.).

Even modest increases of serum total bilirubin concentration may represent the beginning of reduced bilirubin excretion capacity, provided that Gilbert's syndrome and other unrelated causes of bilirubin elevation can be excluded. It is a function of the liver to clear plasma of bilirubin and excrete it into the bile. The late Hyman Zimmerman, in 1978 and again in 1999, after a careful review of clinical trials and literature reports, proposed that the appearance of jaundice in association with drug-induced hepatocellular injury indicated possible mortality in about 10 to 50 percent of patients with that combination (FDA, id., p4.).

Another commonly done test, the blood prothrombin time (or its derivative, Internationalized Ratio, INR) may be useful as a liver function test of protein synthesis. In acute liver failure caused by acetaminophen overdose, increases in INR may precede rises in total bilirubin levels. Thus, only a small decrement in liver function in pre-approval trials may provide a signal that additional and more severe cases may occur when larger numbers of patients are exposed. The full impact of this may not be realized until after a drug's approval for clinical use and marketing.

The condition of cholestasis occurs when bile and bile fluids cannot flow from the hepatocytes to the duodenum. The accumulation of bile salts in hepatocytes can lead to cellular apoptosis, necrosis, and mitochondrial dysfunction (Wolf et al., id., p298.). Cholestasis may result from physical obstructions such as gallstones or tumors, or from metabolic disorders as a result of drugs interfering with BSEP, MDR3, and other transporters.

MDR3 and DILI: MDR3 and BSEP are potentially important targets for drug-induced liver injury. MDR3 is able to transport a number of MDR1 substrates (e.g., digoxin, paclitaxel, and vinblastine), although the contribution of MDR3 clinically is probably less important than other transporters such as MDR1. Verapamil, cyclosporine, and vinblastine are able to inhibit MDR3, explaining why these drugs could adversely affect canalicular phosphatidylcholine secretion (Lang, T., et al. [2006] Genetic variability, haplotype structures, and ethnic diversity of hepatic transporters MDR3 (ABCB4) and bile salt export pump (ABCB11), Drug Metabolism and Disposition, 34(9), 1582-1599. p1582.).

In contrast to xenobiotic transporters such as MDR1 which control the access of substrates to pharmacological sanctuaries, changes in MDR3 and BSEP transport function may have their greatest impact on occurrence, pattern, and prognosis of cholestatic liver injury. Furthermore, they may modulate the individual sensitivity to drug-mediated inhibition of MDR3 and BSEP transport and, consequently, the individual sensitivity to DILI (Lang, id., p1598.).

MDR3 and drug interactions: ABCB4-expressing BRO human melanoma cells exhibit no resistance to a range of drugs including vincristine, colchicine, etoposide, daunorubicin, doxorubicin, actinomycin D, and gramicidin D (Morita & Terada, id., p6.). Vesicles prepared from expression of ABCB4 in yeast confer resistance to aureobasidin A, an antifungal cyclic depsipeptide antibiotic, which is overcome by vinblastine, verapamil and cyclosporine A (Morita & Terada, id., p6.). Smith et al. have reported that polarized monolayers of ABCB4-expressing LLC-PK1 cells show an increased directional transport of several ABCB1 substrates, such as digoxin, paclitaxel, daunorubicin, vinblastine, and ivermectin, and that the transport rate of these drugs except for paclitaxel, is lower in ABCB4-expressing cells than in ABCB1-expressing cells (Smith, id., p23536.). Furthermore, ABCB4-dependent transport of digoxin is inhibited by ABCB1 reversal agents cyclosporine A, valspodar, and veraparnil (Morita & Terada, id., p6.). In addition, expression of ABCB1 or ABCB4 in HEK293 cells decreases the accumulation of rhodamine 123 and rhodamine 6G, and these reductions are more marked in ABCB1-expressing cells than in ABCB4-expressing cells (Morita & Terada id., p6,). The accumulation of BODIPY-verapamil HEK293 cells is strikingly reduced by ABCB1 expression but is not altered by ABCB4 expression, indicating that BODIPY-verapamil is not a transport substrate of ABCB4 but an inhibitor of the ABCB4-mediated phospholipid efflux (Morita & Terada, id., p6.). These findings suggest that ABCB4 cannot cause multidrug resistance due to the low rates of ABCB4-mediated export of drugs compared with ABCB1-mediated export. The nonphospholipid substrates may have lower affinities for ABCB4 than ABCB1 and/or compete with membrane PC for binding to ABCB4. Furthermore, the addition of taurocholate has no effect on the ABCB4-mediated efflux of rhodamine 123 and rhodamine 6G, which may be attributed to sufficient solubility of these substrates in the aqueous medium (Morita & Terada, id., p6.).

The ABC B4-mediated secretion of PC is enhanced by the activation of protein kinase A or C and is decreased by the inhibition of these kinases (Monte & Terada, id., p6.). Itraconazole, an antifungal agent, is known to cause drug-induced cholestasis (DIC) and is associated in a rat model of cholestasis with a significant decrease in biliary phospholipids (Morita & Terada, id., p6.). In additional studies involving ABCB4-mediated efflux of carbon-14 radiolabeled PC from LLC-PK1 cells, the presence of itraconazole decreased the efflux of PC (Morita & Terada, id., p6).

Expression of MDR3 in Sf9 Cells: The MDR3 gene is cloned into baculovirus and expressed in Sf9 insect cells by methods that one skilled in the relevant art would readily understand (Smith, id., p235635.). Vesicle membranes are prepared from the Sf9 insect cells expressing MDR3 following cell disruption homogenizations and centrifugations (Smith, id. p23535.). Vesicle preparations are used in experiments measure PC transport utilizing fluorescence or radiolabeled substrates.

LLC-PK1 cells derived from a pig kidney epithelial cell line are transfected with the MDR3 gene and cultured for use in drug transport assays (Smith, id., p23534.). Transfected LLC-PK1 cells are used in directional transport experiments. However, assays have to be repeated with various batches of cell lines to obtain useful data to compare activities (Smith, id., p23533.).

The current MDR3 export transport assays have many issues including: (1) complexity and variability in preparing inside-out vesicles from transfected insect cell lines; (2) physiological relevance of vesicles prepared from insect cell lines; (3) transfected mammalian cells of different complexities and variable expression and/or activities; (4) requirement of radiolabeled phosphatidylcholine or fluorescence phospholipid precursors; (5) inability to assess the indirect effect of a test agent's metabolism on MDR3 transport; and (6) assays do not, allow exploration of interactions under physiological conditions in which bile salts and other transporters are present. In general, less s known about MDR3 because of the difficulty of establishing a robust activity assay (Ellinger, P., et al. [2013]. Detergent screening and purification of the human liver ABC transporters BSEP (ABCB11) and MDR3 (ABCB4) expressed in the yeast Pichia pastoris. PLoS One 8(4), e60620, p2.).

RATIONALE FOR THE INVENTION

A continued need exists for an in vitro method that can more reliably, routinely, and accurately be used to study in vivo hepatobiliary processes including phosphatidylcholine (PC) export transport and/or formation activity. The method should be adaptable and scalable to modern drug discovery screening paradigms. The method should be flexible to allow investigation of test-agent—derived metabolites on PC export transport and/or formation. The method should be physiologically relevant to allow extrapolation of an in vitro finding to an in vivo situation. The disclosed present subject matter offers the ability to assess the test-agent's effect on PC export transport and/or formation activity. Furthermore, this method offers the potential to reduce the use of animals in preclinical drug development. Finally, the results from this method can be used to predict a test agent's potential for drug-induced liver injury, cholestasis, and drug-drug interactions.

BRIEF DESCRIPTION OF THE INVENTION

The disclosed present subject matter is a method to measure modulation of PC export transport and/or formation activity in hepatocyte or stable cell-line preparations by test agents including but not limited to drugs, drug candidates, biologicals, food components, herb or plant components, amino acids, proteins, peptides, DNA, and RNA. Furthermore, the method is designed to determine the modulation of PC export transport and/or formation activity not only by said drugs, drug candidates, biologicals, food components, herb or plant components, amino acids, proteins, peptides, oligonucleotides, DNA, and RNA, but also further their metabolites or biotransformed products formed in situ. The PC export transport and/or formation activity modulation includes but is not limited to inhibition, induction, activation, and/or regulation. more specifically, an in vitro method is provided using hepatocyte preparations from human and animal livers or stable cell lines from expressing multidrug resistant 3-P glycoprotein (MDR3)—including HepG2, Huh7, and HepaRG—that are incubated with stable isotope- or radioisotope-labeled choline, bile salts, and a test agent to determine the test agent's effect on inhibition, induction, activation, and regulation of PC export transport and/or formation activity. Hepatocyte preparations include: hepatocyte suspensions in incubation buffers and hepatocytes plated on a suitable medium or support. Stable cells lines such as HepG2, Huh7, and HepaRG can also be suspended in a suitable incubation buffer or plated on a suitable medium or support. The hepatocytes can be obtained from freshly prepared human or animal livers or cryopreserved hepatocytes.

Choline used in the method includes but is not limited to deuterium, tritium, carbon-13, and carbon-14 choline. Phosphatidylcholine (PC) includes but is not limited to the PC molecular species 34:2, 34:1, 36:2, 36:1, 36:4, 36:3, and 38:6

The present subject matter furthermore describes procedures, incubation conditions, and cell culture components to maintain and monitor PC export transport and/or formation in hepatocyte preparations, and the means to measure the concentrations of PC. These include but are not limited to the concentration of hepatocytes, the incubation time, the concentrations of bile acid/salt compounds, the concentration of choline, the means to separate extracellular and cellular portions of PC, and the procedures to prepare the cells and perform the incubations. The mean to determine the concentrations of PC include but are not limited to HPLC, mass spectrometry (MS), liquid chromatography mass spectrometry, radioactive counting, and fluorescence.

Furthermore, the present subject matter describes a method that can be used with stable cell preparations derived from cell lines expressing multidrug resistant 3-P glycoprotein (MDR3), including HepG2, Huh, and HepaRG cell lines that are incubated with choline, bile acid/salt compound(s) and test agent to measure a test agent's effect on PC transport and/or formation.

This method is readily adaptable to a variety of high-throughput screening approaches in which hepatocyte preparations or stable cell lines can be used in incubations with choline, bile acid/salt compounds and test agents and post-incubation measurements of PC extracellular and/or cellular concentrations can be determined, An advantage of the present subject matter is its capability to assess test agent's ability to inhibit, induce, activate, and/or regulate PC export transport and/or formation activity without using non-physiological vesicle preparations, Furthermore, the method can be adapted to a variety of incubation preparations including hepatocyte suspension and plating as well as stable cell lines from cell lines expressing multidrug resistant 3-P glycoprotein (MDR3), including HepG2, Huh7, and HepaRG suspensions or plating. The method is not limited to any specific incubation formats such as, for example, size and number of incubation chambers.

Furthermore, the present subject matter can be provided in the form of a kit comprising buffers, reagents, chemicals, choline, bile acids, bile salts, internal standard, incubation platforms, and instructions, which together allow a person skilled in the art to practice the present invention.

Furthermore, the method allows for the ability to assess metabolites derived frog test agents for their potential to inhibit, induce, activate, and/or regulate PC export transport and/or formation activity.

Finally, the presently disclosed method, including the kit, can be used to identify chemicals or biologics that have the potential to cause liver injury, drug-drug interactions, and/or could be used as therapeutic agents for the treatment of cholestasis, abnormality of phosphatidylcholine metabolism, liver disease, and cholesterol abnormality.

DETAILED DESCRIPTION OF INVENTION

Figure 1:
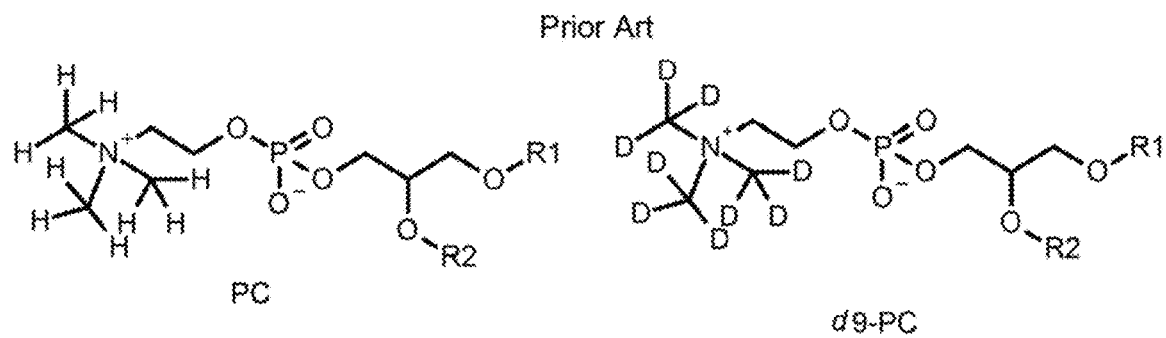
FIG. 1 displays chemical structures of phosphatidylcholine (PC) and d9-PC species where PCs are composed of saturated and/or unsaturated C16-C22 fatty acids conjugated to the glycerol moiety.

In relation to the presently disclosed subject matter, a novel method is provided for measuring a test agent's ability to modulate mammalian phosphatidylcholine (PC) export transport and/or formation activity in preparations of human and animal hepatocytes or in stable hepatic-derived cell lines such as HepG2, Huh7, and HepaRG by incubation of stable isotope- or radioisotope-labeled choline, bile acid/salt compound or compounds, and the said test agent in said preparations, followed by measuring extracellular and/or cellular PC concentrations post-incubation. The test agents used in the present invention include but are not limited to drugs, drug candidates, biologicals, food components, herb or plant components amino acids, proteins, peptides, oligonucleotides, DNA, and RNA. Interference with PC export transport and/or formation is associated with drug-induced liver injury (DILI). The PC export transport and/or formation activity modulation includes but is not limited to inhibition, induction, activation, and/or regulation. Furthermore, the method allows for a test agent-derived metabolite(s) to be tested for modulation of PC export transport and/or formation activity. The present invention can be provided in the form of a kit comprising buffers, reagents, chemicals, stable isotope- or radioisotope-labeled choline, bile acid/salt compounds, internal standard, incubation platforms, paper and/or electronic instructions, and additional materials necessary to allow a person skilled in the art to practice the present invention.

Furthermore the presently disclosed invention to measure a test agent's ability to modulate PC export transport and/or formation can be used by a person skilled in the art as a drug discovery screen for testing said agent's potential to cause liver injury, drug-drug interactions, and/or potential as a therapeutic for purposes of treating a condition such as cholestasis, abnormality of PC metabolism, and liver disease. Even further, the present invention can be used as part of a drug discovery-screening paradigm.

Unless defined otherwise, all technical and scientific terms used herein have the meaning commonly understood by a person skilled in the art to which this invention belongs. The meaning and scope of terms should be clear; however, in the event of any latent ambiguity, definitions provided herein take precedent over any dictionary or extrinsic definition. In this application, the use of "or" means "and/or" unless stated otherwise. Furthermore, the use of the term "including" as well as other forms of same such as includes and "included" is not limiting. With reference to the use of the words "comprise" or "comprises" or "comprising" in this patent application Applicants note that unless the context requires otherwise, those words are used on the basis and clear understanding that they are to be interpreted inclusively, rather than exclusively, and that Applicants intend each of those words to be so interpreted in construing the patent application, including the claims.

As used in the specification and claims, the singular form "a," "an," and "the" include plural references unless the context clearly dictates otherwise.

In this disclosure, "comprise," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Where a range of values is provided, it is understood that each intervening value, to the tenth of the unit of the lower limit, unless the context clearly dictates otherwise, between the upper and lower limit of that range and any other stated or intervening value in that stated range, is encompassed within the invention. The upper and lower limits of these ranges may independently be included in the smaller ranges and are also encompassed within the invention, subject to any specifically excluded limit in the stated range. Where the stated range includes one or both of the limits, ranges excluding either or both of those included limits are also included in the invention.

Hepatocytes have specific membrane domains that one skilled in the art would recognize and include but are not limited to an apical (canalicular) membrane or domain and a basolateral (blood or sinusoidal domain) membrane or domain. The hepatocyte basolateral membrane or domain is involved in the uptake into the cell of drugs and xenobiotics, while the apical membrane or domain provides a route for intracellular-produced PC to be excreted or transported out of the cell into the bile flow. The transport of PC out of hepatocytes into bile primarily involves transporter proteins located on the cell's apical membrane.

ATP-binding cassette (ABC) transporters constitute one of the largest families of membrane transport proteins and can transport a wide range of different substrates ranging from small ions to large proteins across biological membranes using ATP as an energy source (Ellinger, id., p1.). In hepatocytes, eleven ABC transporters are expressed including three ABC transporters involved in bile formation—BSEP (ABCB11), MDR3 (ABCB4), and ABCG5/8 (Ellinger, id., p1.), Of the transporters in the apical or canalicular domain of hepatocytes is the transporter protein named multidrug resistance protein 3 (MDR3) encoded with the A8C84 gene. MDR3 is also called PC floppase or ABCB4 or multi rug-resistant 3 P-glycoprotein (Lang, id., p1.). Earlier studies show that MDR2 is identical in sequence to MDR3. Abcb4 in animals, formerly known as Mdr2, is the homolog of human ABCB4. MDR3 is mainly expressed in the liver and localized in the canalicular membranes of hepatocytes. It is primarily responsible for the secretion of phospholipids into bile. MDR3 is one of the main transporters in human hepatocytes involved in bile formation.

Interference in MDR3 function can lead to impaired hepatobiliary secretion of PC. Genetic defects or mutations in MDR3 that interfere with hepatobiliary secretion of PC are associated with several diseases, including progressive familial intrahepatic cholestasis type 3 (PFIC3); benign recurrent intrahepatic cholestasis type 3 (BRIC3), intrahepatic cholestasis of pregnancy (ICP), low-phospholipid-associated cholelithiasis (LPAC), primary biliary cirrhosis, and cholangiocarcinoma. In the case of PFIC3, the condition has been associated with one or more polymorphisms in the genetic code for MDR3 leading to inadequate MDR3 function and associated liver injury. PFIC3 is characterized by progressive liver damage usually requiring transplantation, while BRIC3 is characterized by intermittent and non-progressive cholestasis.

In the presently disclosed subject matte PC export transport is used as a marker for MDR3 and/or any additional PC transporters or floppases involved in the excretion of PC from hepatocytes.

In modern drug discovery and development, assessing the potential of a drug candidate to produce clinical drug-induced liver injury (DILI) or drug-drug interaction is a major issue. Several drugs have reached marketing approval by the Food and Drug Administration in the United States to later be found to produce unexpected DILI. The extremely low rate of BILI, in some cases at rates estimated to be about 1 in 10,000, have limited the utility of clinical trials, with patient populations in the hundreds to low thousands, to predict this adverse reaction. Preclinical animal models and toxicity studies often do not show any evidence of DILI. Therefore, drug discovery and development scientists have tried to develop in vitro models to predict a drug's potential to produce DILI. Most of these methods focus on the formation of reactive metabolites, a drug's effects on hepatic mitochondrial function and the potential for drug-induced apoptosis (programmed cell death). These methods are highly complex and difficult to interpret, which limits their utility as a drug-discovery screening approach.

Recently, greater implication of DILI as the result of interference with PC export has been recognized. As mentioned above, it has now been demonstrated that several drugs known to cause DILI have been found to interfere with PC transport out of hepatocytes. DILI toxicities include cellular mitochondrial damage, apoptosis (programmed cell death), and necrosis. The result of the toxicity can be cholestasis a condition in which bile cannot flow from the liver to the duodenum. The ultimate result of DILI can be the need for liver transplantation.

The need for model systems and methods to assess a drug's and test agent's ability to interfere with PC export transporters has led to the development of several in vitro approaches including ABCB4-expressed insect cell vesicle platforms and ABCB4 transfected cells. As described above, each of these methods has drawbacks including unreliability, difficulty in preparation of test systems, inability to incorporate into drug discovery paradigms, false positives and negatives, and lack of extrapolation to human hepatic function.

Therefore, there exists a need to develop a method that can be used by one skilled in the art to accurately and reliably measure a test agent's ability to modulate PC export transport and/or formation activity. Furthermore, the method should be flexible to allow for studies of a variety of test agents and should offer the potential to assess test agent-derived metabolites for their ability to modulate PC export transport and/or formation activity. Furthermore, the method should be readily adaptable for several different types of hepatocyte incubation preparations, including human and animal. The method should offer the potential to be used with stable cell lines expressing multidrug resistant 3-P glycoprotein (MDR3), including HepG2, Huh7, and HepaRG. The method should minimize or not require the use of radiolabeled chemicals to measure PC export transport and/or formation. Even further, the method should be adaptable to drug discovery screens and utilize incubation platforms that allow a test agent to be screened at appropriate concentrations and incubation periods.

The present disclosed subject matter provides a method to measure modulation of transport and formation of PC produced in hepatocyte preparations comprising incubation of stable isotope- or radioisotope-labeled choline in the presence or absence of bile salts or acids with or without a test agent in said hepatocyte preparations. Post-incubation concentrations of formed PC present in extracellular and/or cellular media are measured and used to assess test agent modulation of PC export transport and/or formation activity, Test agents include but are not limited to drug, drug candidate, biological, food component, herb or plant component, amino acid, peptide protein, oligonucleotide, DNA, and RNA. A person skilled in the art would realize that the test agent could be added to the incubation medium in an appropriate solvent or buffer.

Choline used in the method includes but is not limited to deuterium-(1 to 13 deuterium atoms), tritium-, carbon-13 (1 to 5 carbon-13 atoms), and carbon-14 labeled choline. Bile acids and salts used in the method include but are not limited to cholic acid, chenodeoxycholic acid, deoxycholic acid, lithocholic acid, and their respective glycine and taurine conjugates individually or in combinations.

The PC export transport and/or formation activity can be inhibition, induction, activation, or regulation. Inhibition refers to a decrease in PC export transport and/or formation, and can be competitive, non-competitive, un-competitive, or irreversible. Induction refers to an increase in hepatic proteins responsible for PC export transport or formation. Activation refers to the process whereby the test agent would increase the functional activity of the proteins involved in PC export transport and/or formation. Regulation refers to controlling the rates of PC export transport and/or formation.

Incubations can be conducted using freshly prepared hepatocytes or cryopreserved hepatocytes obtained by standard methods from human and animal livers that one skilled in the art would be well aware of and able to use. The hepatocytes can be used in the form of suspensions or plated on a suitable culture plate containing appropriate growth medium.

In place of hepatocytes, a person skilled in the art could use a stable cell line expressing multidrug resistant 3-P glycoprotein (MDR3), including HepG2, Huh7 and HepaRG. HepG2 is a perpetual cell line derived from the liver of a 15-year-old. Caucasian male with a ell-differentiated hepatocellular carcinoma. Because of the high degree of morphological and functional differentiation in vitro, HepG2 cells can be a suitable model to study the intracellular trafficking and dynamics of bile canalicular and sinusoidal membrane proteins and lipids in human hepatocytes in vitro (Ihrke G., et al. [1993]. WIF-B cells: an in vitro model for studies of hepatocyte polarity. J Cell Biol, 123(6 Pt 2), 1761-1775, p1761.). Huh-7 is a well differentiated hepatocyte-derived cellular carcinoma cell line that was originally taken from a liver tumor in a 57-year-old Japanese male in 1982 (www.huh7.com). HepaRG cells are terminally differentiated hepatic cells derived from a human hepatic progenitor cell line that retains any characteristics of primary human hepatocytes (www.heparg.com).

Presently disclosed is a novel method and embodiments for measuring the modulation of PC export transport and/or formation activity by a test agent whereby incubations of hepatocytes from mouse, rat, dog, rabbit, monkey, and human are carried out at concentrations ranging from about 0.001 to about 1.0 million cells/mL and can be conducted in 96-well plates with about 0.01 to about 1000 µg/mL of stable isotope- or radiolabeled-choline in the presence or absence of bile acids or salts at 0.01 µM to about 10,000 µM in Williams E buffer in the presence or absence of test agents at concentrations ranging from about 0 µM to about 1000 µM at 37° C. under 5% $CO_2$ for 0.1 to 72 hours. After incubation, the 96-well plate is centrifuged at 4000 RPM for 15 minutes at room temperature. The supernatant is removed from the cell pellet and labeled as extracellular media. Alternatively, after incubation, the cell suspension is filtered with a pore size range from about 0.2 to about 5 µm. The 4000 RPM supernatant (extracellular media) is mixed with 1-3 times the volume organic solvent, such as isopropanol, methanol, and/or acetonitrile, and the resultant mixture is centrifuged at 4000 RPM for 20 minutes at 4° C. An internal standard suitable for liquid chromatography mass spectrometry measurements of PC species is added to the organic solvent.

The hepatocyte cell pellet is re-suspended in water, Williams E buffer or other buffer system, and subjected to a standard freeze-thaw procedure and sonication to detach cells. The cell suspension is mixed with 1-3 times volume of hexane:isopropanol (9:1 in volume), and followed by centrifugation at 4000 RPM for 10 min. The hexane:isopropanol phase is collected and dried under nitrogen. The residues are reconstituted in 200 µL isopropanol. An internal standard suitable for liquid chromatography mass spectrometry measurements of PC species is added to the hexane:isopropanol solution. Alternately, the hepatocyte cell pellet can be directly treated with hexane:isopropanol (9:1 in volume) followed by centrifugation at 4000 RPM for 10 min.

Measurement of PC species in the extracellular media and/or cellular contents can be accomplished by using standard liquid chromatography mass spectrometry with multiple reaction monitoring (MRM) of specific ions associated with PC species. Quantitation of PC in intracellular and cellular media is performed using, standard curves prepared from reference PC species.

Following quantitation of selected PC species in the extracellular and cellular media, calculation is made of PC export transport and/or formation activity. In the case of PC export transport activity, the concentration of the measured PC in the extracellular media is divided by the hepatocyte cell concentration and the length of incubation. This relates to the amount of PC transported into the extracellular media during the course of incubation. The selection of PC species to measure is based on the formation of PC species in the incubation. In general, PC 34:2 is measured.

PC formation activity is calculated by first determining the total PC formed for each species in the incubation. This is determined by adding the amount of PC in the extracellular media to the amount in the intracellular media. The total PC amount for each species is then divided by the hepatocyte cell concentration and the length of incubation.

The effect of a test agent in terms of percentage (%) of inhibition on PC export transport and/or formation activity is determined by the following equation:

$$\% \text{ Inhibition} = \frac{(\text{Activity without Test Agent} - \text{Activity with Test Agent}) \times 100}{(\text{Activity without Test Agent})}$$

In one embodiment of the disclosed subject matter, incubations of hepatocytes from mouse, rat, dog, rabbit, monkey, and human are carried out at concentrations ranging from about 0.001 to about 1 million cells/mL and can be conducted in 96-well plates with about 0.01 to about 1000 µg/mL d9-choline in the presence of 0.01 to 10000 µM taurocholic acid in Williams E buffer in the presence or absence of test agents at concentrations ranging from about 0.01 µM to about 1000 µM at 37° C. under 5% $CO_2$ for about 0.1 to 72 hours.

In yet another embodiment of the disclosed subject matter, incubations of hepatocytes from mouse, rat, dog, rabbit, monkey, and human at concentrations ranging from about 0 to about 025 million cells/mL can be conducted in 96-well plates with about 0 µM to about 100 µg/mL d9-choline in the presence of taurocholic acid in Williams E buffer in the presence or absence of test agents at concentrations ranging from about 0.01 µM to about 1000 µM at 37° C. under 5% $CO_2$ for about 2 hours.

In even yet another embodiment of the disclosed subject matter, incubations of hepatocytes derived from human and animal liver at concentrations ranging from about 0 to about 0.25 million cells/mL can be conducted in 96-well plates with about 100 µg/mL d9-choline in the presence of taurocholic acid in Williams E buffer in the presence or absence of test agents at concentrations ranging from about 0.01 µM to about 1000 µM at 37° C. under 5% $CO_2$ for about 2 hours.

In another embodiment of the method, one skilled in the art would appreciate that the investigator can practice the method with hepatocytes prepared from human and animal livers. Animal include mouse, rat, dog, rabbit, and monkey. Hepatocytes can be prepared from individual livers or be prepared as a pooled sample of hepatocytes derived from multiple different human or animal livers.

In another embodiment, a person skilled in the art would recognize that the method is not limited to 96-well plates but can readily be modified for use with a variety of incubation platforms including a Petri dish with cells plated in a monolayer, a single-well plate, or a multi-well plate format.

In yet another embodiment, one skilled in the art would readily recognize that PC formed in the present method can be separated from the extracellular and cellular media by a variety of techniques including but not limited to centrifugation; filtration; solid phase extraction with C18, C8, C4 or anion exchange solid support; by liquid-liquid extraction; or by addition of acetonitrile, methanol, or any suitable solvent, followed by centrifugation or filtration.

A person skilled in the art would recognize that additional methods for quantitation of PC are available to the investigator that include but are not limited to high-performance liquid chromatography (HPLC), mass spectrometry, radioactivity counting, enzyme assay and/or fluorescence.

An additional embodiment of the presently disclosed method can be practiced to investigate a test agent's effect on absorption, distribution, metabolism, and excretion (ADME)-related processes. As one skilled in the art would readily recognize, the method can be used to allow for the measurement of test-agent—derived metabolites to, inhibit, induce, activate, and/or regulate PC export transport and/or formation, In yet another embodiment of the method, it can be modified whereby selective drug metabolizing enzyme inhibitors can be co-incubated with test agents to measure the effect on PC export transport and/or formation.

In another embodiment, one skilled in the art would appreciate that the method can be practiced to allow for measurement of interactions between a test agent and known modulators of PC export transport and or formation.

In another embodiment, the method can be used with human and/or animal hepatocytes that have ADME enzyme phenotypes, which can allow for measuring the effect of specific hepatic phenotype on a test agent's modulation of PC export transport and/or formation. For example, hepatocytes derived from a human liver expressing a genetic polymorphism deficiency in cytochrome P450 2D6 enzyme activity can be practiced in the method to measure a test agent's modulation on PC export transport and/or formation.

As one skilled in the art would appreciate the present method can be used as a drug discovery-screening assay to measure the effect of multiple test agents on PC export transport and/or formation activity. The assays can include known inhibitors and non-inhibitors of PC transport. Results from the screening assay can be used for selection or ranking of test agent's modulation of PC export transport and/or formation. Furthermore, the method can be practiced to determine in vitro $IC_{50}$ values for test agents. Additionally, the results can be used as part of in vitro-in vivo correlation of a PC transport activity profile.

The presently disclosed subject matter for the method to measure a test agent's modulation of PC export transport and/or formation activity and embodiments can be practiced to identify chemicals or biological test agents that have the potential to cause liver injuries, drug-drug interactions, and/or can be used as therapeutic agents for the treatment of cholestasis, abnormality of bile salt metabolism, liver diseases, and cholesterol abnormality.

The presently disclosed subject matter and embodiments can be provided in the form of a kit comprising buffers, reagents, chemicals, stable isotope- or radioisotope-labeled choline bile acids, bile salts, internal standard, incubation platforms, and instructions that together allow a person skilled in the art to practice the instant disclosure.

The references cited in the specification are incorporated herein by reference to the extent that they supplement or explain, or provide a background for or teach methodology, techniques, and/or compositions employed herein.

Abbreviations: ABC transporters: ATP binding cassette transporters; ADME: absorption, distribution, metabolism and excretion; BIRC2: benign recurrent intrahepatic cholestasis type 2; PC: phosphatidylcholine; HPLC: high performance liquid chromatography; LC/MS/MS: liquid chromatography coupled with a tandem mass spectrometry; MDR3: multidrug resistance protein 3 or multidrug-resistant 3 P-glycoprotein; MRM: multiple ion monitoring; PFIC2: progressive familial intrahepatic cholestasis type 2.

EXAMPLES

The following examples have been included to illustrate the representative modes of the invention. One of ordinary skill in the art will appreciate that the following examples are intended to be representative only and that additional variations and modifications can be employed without departing from the spirit and scope of the presently disclosed subject matter.

Experimental Procedures:

Unless specifically stated otherwise, following experimental procedures were applied.

Chemicals and Biochemicals: d9-Choline was purchased from Cambridge Isotope Laboratories Inc (Tewksbury, Mass.). Mouse, rat, dog, monkey, rabbit, and human hepatocytes and InVitroGRO HT medium were obtained from BioreclamationIVT (Baltimore Md.). Williams Medium E was purchased from GIBCO. Other reagents were purchased from Sigma-Aldrich (St. Louis, Mo.) unless stated otherwise in the text.

Preparation of hepatocytes: Functional hepatocytes to be employed in any variation of the present. PC export transport and/or formation activity assay can, as one skilled in the art would be well aware, be derived from cryopreserved hepatocytes (stored in liquid nitrogen) or hepatocytes freshly prepared from liver, and may be co-cultured with other cell types such as stromal cells and Kuffer cells. Hepatocytes should have high cell viability (>80%), high activity to form PC, and high activity to transport PC.

Fifty mL InVitroGRO HT medium was pre-warmed in a 37° C. water bath. A vial of hepatocyte s removed from a liquid $N_2$ tank and quickly warmed in a 37° C. water bath by holding in hand with slow rotation. As soon as the edge of the frozen cells was separated from the wall of the vial, the frozen cells were poured into the pre-warmed HT medium and the remaining cells in the vial were collected using pipette. The tube was centrifuged at 50 g, 25° C. for 5 minutes, the supernatant was removed and the cell pellet was re-suspended in 8 mL of pre-warmed Williams E buffer, the cell numbers were counted in a hemocytometer. The yield was $1 \times 10^6$ cell mL. The cells were counted in 0.4% Trypan blue (80 µL Williams E buffer+10 µL Trypan blue stock 10 µL cells). The hepatocyte concentration was adjusted with Williams E buffer to meet the objectives of various experiments.

LC/MS/MS assays: Liquid chromatography was carried out using a Shimadzu (Columbia, Md.) HPLC system consisting of an SCL-10Avp system controller, two LC-10ADvp pumps, a CTC HTC PAL autosampler, a Shimadzu SPD-10ADvp UV detector and an automated switching valve. The switching valve was used to divert the column effluent to either waste or to the MS instrument. The Shimadzu HPLC system was used for sample injection and analyte separation. Each sample was loaded onto a reverse phase column, Phenomenex (Torrance, Calif.) Luna C8 5 µ2 mm×50 m. The column chamber's temperature was ambient. The initial HPLC mobile phase conditions used for separation and elution of analytes comprised 50% acetonitrile in water containing 0.1% formic acid (A) and isopropanol:acetonitrile (9:1) (B). The flow rate was 0.5 mL/min. The amount of B in the mobile phase was ramped linearly up to 62% over a 0.5-minute period followed by a slow increase to 63% B in 4.5 minutes, then a rapid increase to 95% B in 0.1 min. After holding at 95% B for 2.3 minutes, the mobile phase was reset to the initial conditions in 0.1 minute, The analytical column was equilibrated with the starting mobile phase for 2.5 minutes. The total run time for each sample analysis was approximately 10 minutes.

The HPLC elute was injected in to an AB Sciex API4000 LC/MS/MS system (Framingham, Mass.) equipped with a Turbo IonSpray source set with a desolvation temperature of 450° C. Nitrogen was used as curtain gas, nebulizer gas heater gas, and collision gas. Data for PC was acquired in the positive ion mode using multiple reaction monitoring methods (MRM). The ion transitions of the MRM method for specific detection of PC species were developed in standard fashion. Ionspray voltage was set at 4000 V and the collision gas (CAD) set at 6. Declustering potential and collision energy was set at 50 and 42 respectively for PC. The PC species were monitored using the following transitions: 768→193, 770→193, 796→193, 798→193, 792→193, 794→193, 816→193. (S)-(+)-Methyl 2-(4,5,6,7-tetrahydrothieno[3,2-c]pyridin-5-yl)-2-(2-chlorophenyl) acetate hydrogensulfate was used as an internal standard with the following ion transition: 322.2→152.1. Propane-1-sulfonic acid {3-[5-(4-chlorophenyl)-1H-pyrrolo [2,3-b]pyridine-3-carbonyl]-2,4difluoro-phenyl}-amide was also used as an internal standard with the following ion transition: 490.1→383.1.

Data analysis: Extracellular concentrations of PC were determined by LC/MS/MS MRM analysis of the 4000 RPM supernatant fractions post-incubation. Cellular concentrations of PC were determined by LC/MS/MS MRM of the extracts of hepatocytes post incubation. PC, export transport and/or formation activity and test agent percent inhibition were calculated using the following equations:

$$PC\ Export\ Transport\ Activity = \frac{(Extracellular\ Concentration\ PC)}{(Hepatocyte\ Concentration) \times (Incubation\ Time)}$$

$$Total\ PC\ amount = Extracellular\ amount + Cellular\ amount$$

$$PC\ Formation\ Activity = \frac{(Total\ PC\ amount)}{(Total\ number\ of\ hepatocytes) \times (Incubation\ Time)}$$

$$\%\ Inhibition = \frac{(Activity\ without\ Test\ Agent - Activity\ with\ Test\ Agent) \times 100}{(Activity\ without\ Test\ Agent)}$$

Kinetic parameters were calculated using standard Michaelis-Menten kinetics, $IC_{50}$ values were determined using Prism software (La Jolla, Calif.) or median-effect equation (Chou, T. C., et al, [2006] Theoretical basis, experimental design, and computerized simulation of synergism and antagonism in drug combination studies. Pharmacol Rev, 58(3), 621-681.).

Example 1

Formation and transport of d9-PC in hepatocytes: Hepatocytes from mouse, rat, dog, rabbit, monkey, and human were prepared in Williams E buffer at concentrations ranging from 0.1 to 0.5 million cells/mL. The hepatocytes in suspension or plated in cell culture plates were incubated with d9-choline at 100 µg/mL in the presence of 0.1-10 mM taurocholic acid in the final volume of 100 µL at 37° C. under 5% $CO_2$ for 1-2 hours. Experiments were carried out in triplicate or duplicate. Suspensions were then centrifuged at 4000 RPM for 15 minutes at room temperature. The 4000 RPM supernatants were mixed with 3× volume isopropanol and the mixtures were centrifuged at 4000 RPM for 20 minutes at room temperature. The supernatants were analyzed by LC/MS/MS for PC species. The hepatocyte cell pellets were re-suspended in 100 µl. Williams E buffer and subjected to a standard, freeze-thaw procedure and sonication to detach cells. The re-suspended cell suspensions were mixed in 3× volume hexane:isopropanol (9:1) solution followed by centrifugation at 4000 RPM for 10 minutes. The organic phase was collected and dried under $N_2$. The residues were reconstituted with 200 µL isopropanol for LC/MS/MS analysis of PC species.

Figure 2:
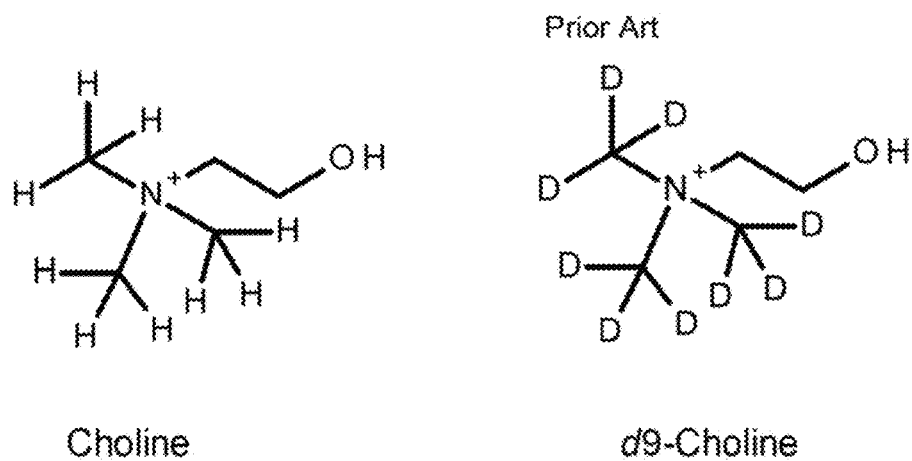
FIG. 2 displays chemical structures of choline and d9-choline.
Figure 3:
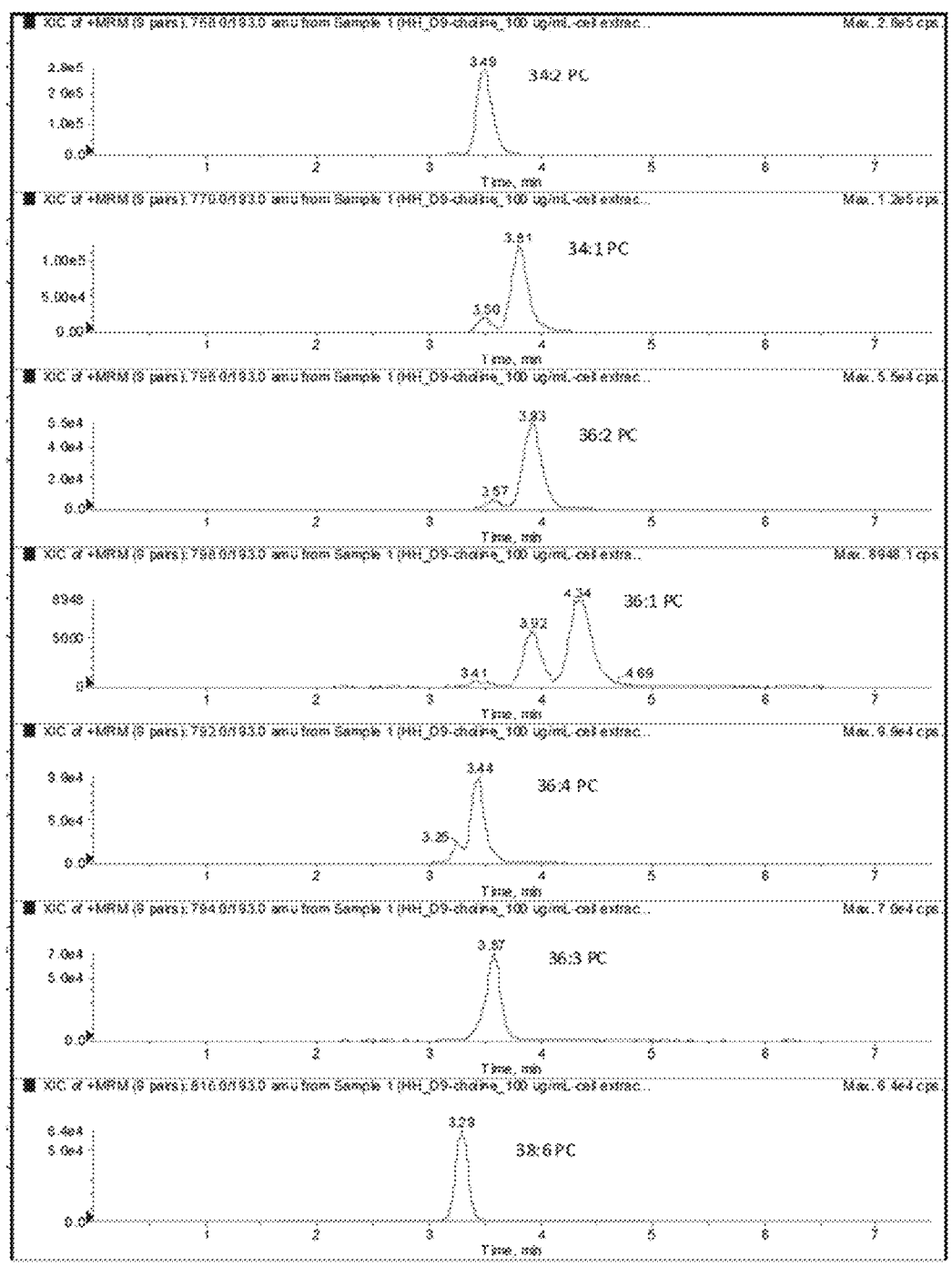
FIG. 3 displays LC-MS chromatograms of d9-phosphatidylcholine (PC) species formed in human hepatocytes. Human hepatocytes were incubated in Williams E buffer at 37° C. for 2 hours in the presence of d9-choline and taurocholic acid at concentrations discussed in the methods. Lipids were extracted from hepatocytes with isopropanol:hexane (9:1).

The chemical structures of d9-PC molecular species and d9-choline are shown in FIGS. 1 and 2. Through in situ synthesis in hepatocytes, d9-choline was incorporated into PC (FIG. 3). Several d9-PC species were formed at various amounts in human hepatocytes, containing saturated and/or unsaturated fatty acids. The major PC species include 34:2, 34:1. 36:2, 36:1, 36:4, 36:3, and 38:6 (Table 1), The PC 34:2 was the most abundant among all the PC species detected. These major PC species were also formed in hepatocytes from rat, dog, and monkey.

Figure 4:
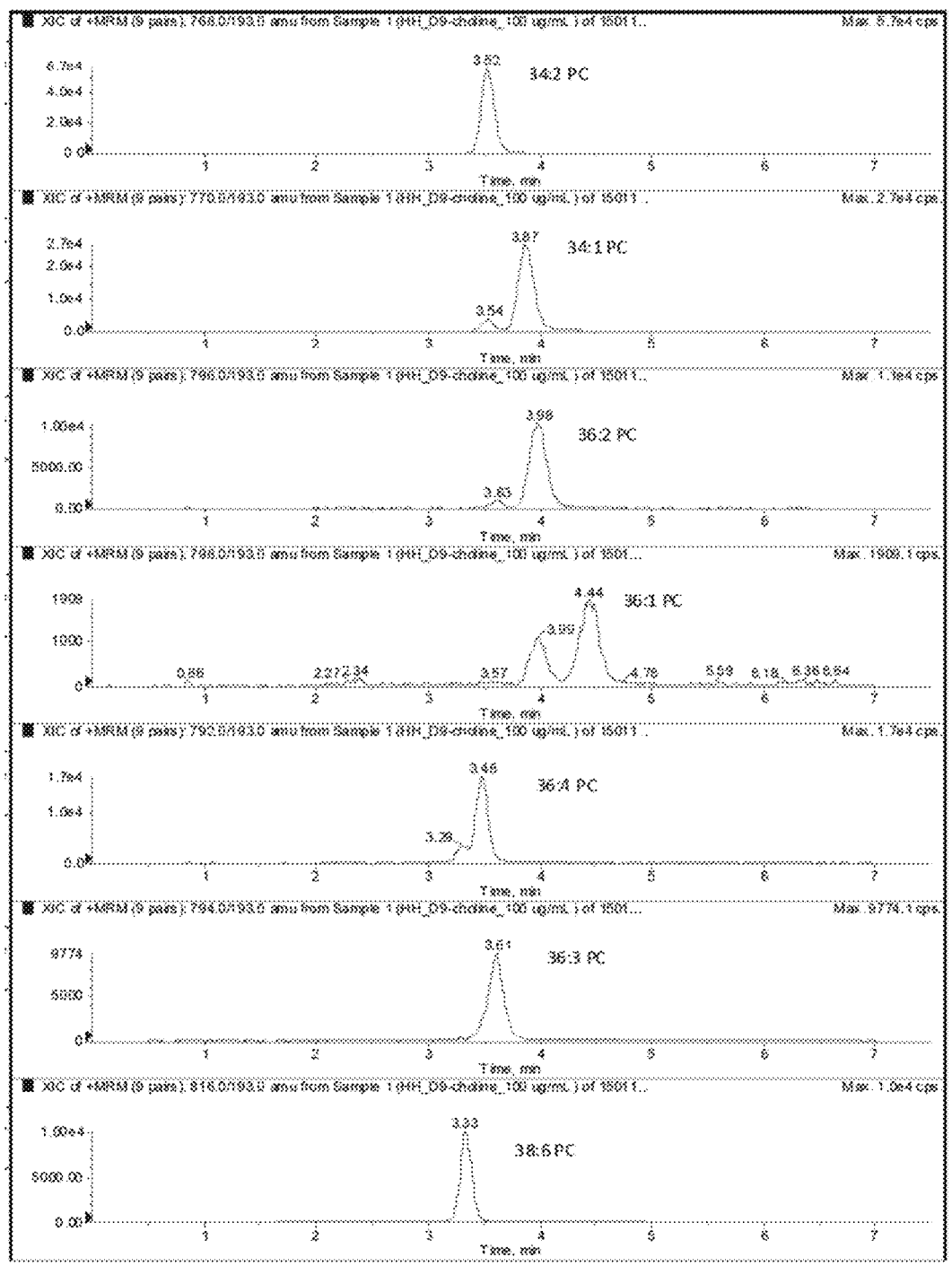
FIG. 4 displays LC-MS chromatograms of d9-phosphatidylcholine (PC) species transported into extracellular medium from human hepatocytes. Human hepatocytes were incubated in Williams E buffer for 2 hours in the presence of d9-choline and taurocholic acid at concentrations discussed in the methods. Cell-free mediums were mixed with isopropanol for LC/MS/MS analysis.

PC species detected in extracellular medium are shown in FIG. 4 and Table 1. The PC 34:2 is most abundant among all these detected PC species. This in vitro PC species profile is consistent with the profile of human bile (Gauss, A, et al. [2013]. Biliary phosphatidylcholine and lysophosphatidylcholine profiles in sclerosing cholangitis. World J Gastroenterol, 19(33), 5454-5463.). Similar results were observed with hepatocytes from rat, dog, and monkey.

TABLE 1

Phosphatidylcholine (PC) molecular species formed in and transported out of hepatocytes in the presence of d9-choline.

| PC Molecular Species | Unlabeled MW* | d9-Labeled MW** | m/z^ |
|---|---|---|---|
| 34:2 | 758 | 767 | 768 |
| 34:1 | 760 | 769 | 770 |
| 36:2 | 786 | 795 | 796 |
| 36:1 | 788 | 797 | 798 |
| 36:4 | 782 | 791 | 792 |
| 36:3 | 784 | 793 | 794 |
| 38:6 | 806 | 815 | 816 |

*Expected molecular weight of the PC species;
**d9-tabeled molecular weight of the PC species
^m/z Values detected by LC/MS/MS in positive ionization mode Example 2

Effect of d9 choline concentration on the formation of d9-PC in hepatocytes: Human hepatocytes at about 0.25 million cells/mL were incubated with d9-choline in the presence of 0.5-5 mM taurocholic acid in Williams E buffer at various concentrations ranging from 0-1000 μg/mL in the final volume of 100 μL at 37° C. under 5% $CO_2$ for 1-2 hours. Experiments were carried out in triplicate or duplicate. Suspensions were then centrifuged at 4000 RPM for 15 minutes at room temperature. The 4000 RPM supernatants were mixed, with 3× volume acetonitrile, and the mixtures were centrifuged at 4000 RPM for 20 minutes at 4° C. The supernatants were analyzed by LC/MS/MS for PC species. The hepatocyte cell pellets were re-suspended in Williams E buffer and subjected to a standard freeze-thaw procedure and sonication to lyse cell membranes. The re-suspended cell suspensions were mixed to 3× volume hexane:isopropanol (9:1) solution followed by centrifugation at 4000 RPM for 10 min. The organic phase was collected and dried under $N_2$. The residues were reconstituted with 200 μL isopropanol for LC/MS/MS analysis of PC species.

Figure 5:
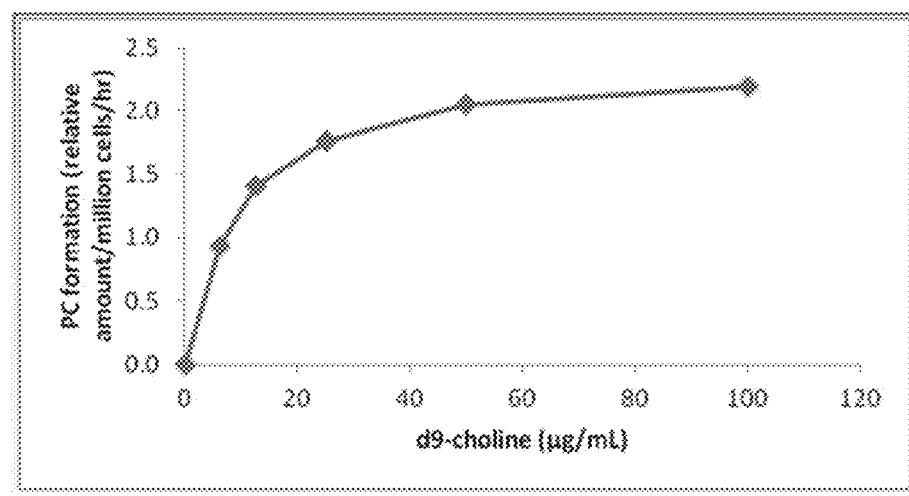
FIG. 5 displays the effect of d9-choline concentration on the formation of d9-phosphatidylcholine (PC, 34:2) in human hepatocytes. Human hepatocytes were incubated in Williams E buffer at 37° C. for 2 hours, in the presence of d9-choline and taurocholic acid at concentrations discussed in the methods. Lipids were extracted from hepatocytes with isopropanol:hexane (9:1).

The incorporation of d9-choline into d9-PC through in sits, synthesis in hepatocytes was related to the concentration of c19-choline (FIG. 5). The incorporation followed Michaelis-Menten kinetics.

Example 3

Time courses for transport of d9-PC in hepatocytes: Hepatocytes at about 0.25 million cells/mL were incubated with 100 μg/mL d9-choline in the presence of 0.5-5 mM taurocholic acid in Williams E buffer in the final volume of 100 μL et 37° C. under 5% $CO_2$ for various times ranging from 0-2 hours. Experiments were carried out in triplicate or duplicate. Suspensions were then centrifuged at 4000 RPM for 15 minutes at room temperature. The 4000 RPM supernatants were mixed with 3× volume isopropanol, and the mixtures were centrifuged et 4000 RPM for 20 minutes at 4° C. The supernatants were analyzed by LC/MS/MS for PC species.

Figure 6:
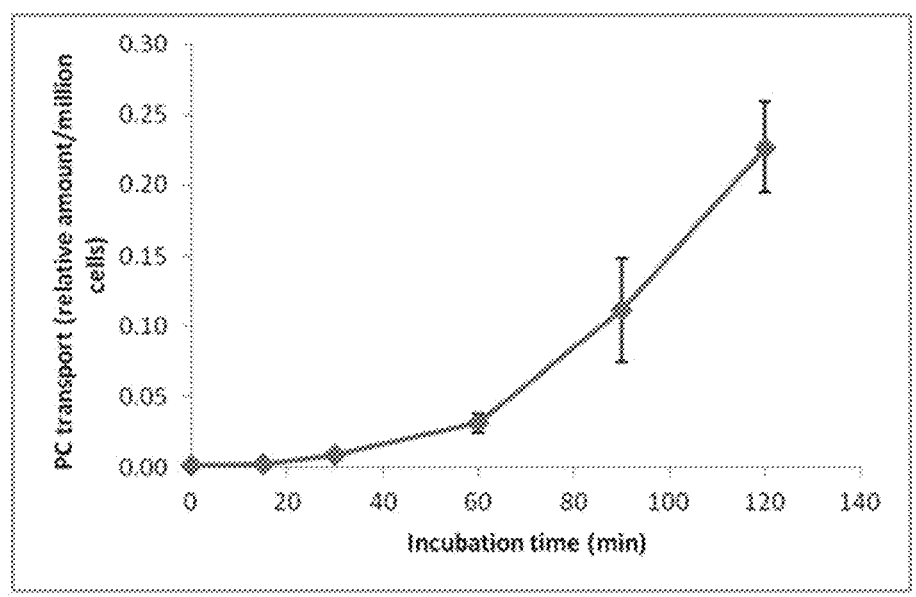
FIG. 6 displays time course for efflux transport of phosphatidylcholine (PC, 34:2) from human hepatocytes. Human hepatocytes were incubated in Williams E buffer for various times in the presence of d9-choline and taurocholic acid at concentrations discussed in the methods. Cell-free mediums were mixed with isopropanol containing analytical internal standard for LC/MS/MS analysis.

The transport of PC was increased when the incubation time increased from 0 to 2 hours, which appeared to be approximately linear between 60 and 120 minutes (FIG. 6).

Example 4

Effects of hepatocyte density on transport of d9-PC: Hepatocytes were prepared in suspension in Williams E buffer at concentrations ranging from 0 to 1 million cells/mL. After pre-incubation in a 96-well plate for 10 minutes at 37° C. under 5% $CO_2$, the hepatocyte suspensions were incubated with d9-choline at 100 μg/mL in the presence of 0.5-5 mM taurocholic acid in the final volume of 100 μL at 37° C. under 5% $CO_2$ for 1-2 hours. Experiments were carried out in triplicate or duplicate. Suspensions were then centrifuged at 4000 RPM for 15 minutes at room temperature. The 4000 RPM supernatants were mixed with 3× volume isopropanol, and the mixtures were centrifuged at 4000 RPM for 20 minutes at room temperature. The supernatants were analyzed by LC/MS/MS for PC species.

Figure 7:
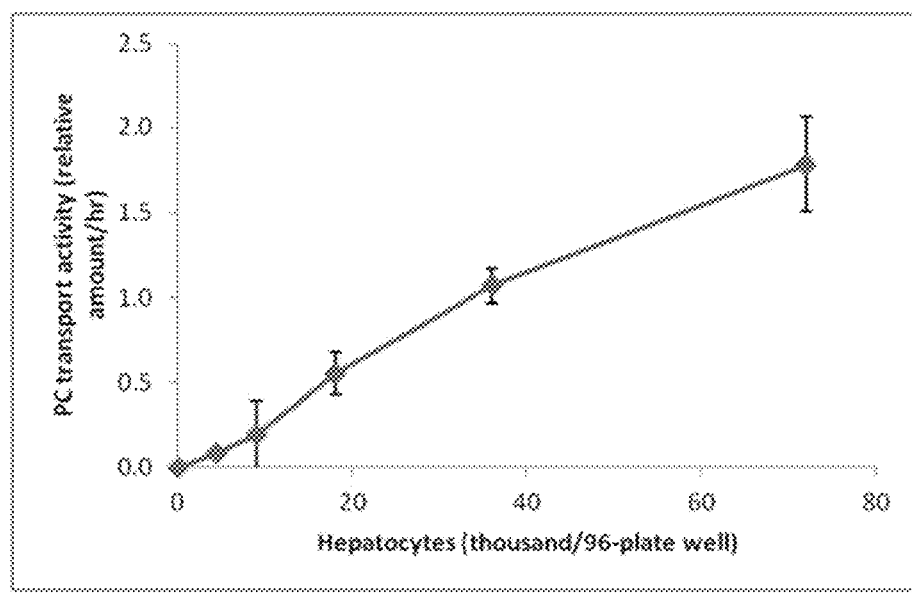
FIG. 7 displays the effect of hepatocyte concentration on the efflux transport of phosphatidylcholine (PC, 34:2) from human hepatocytes. Human hepatocytes were incubated in Williams E buffer for 2 hours in the presence of d9-choline and taurocholic acid at concentrations discussed in the methods. Cell-free mediums were mixed with isopropanol containing the analytical internal standard for LC/MS/MS analysis.

The transport of d9-PC activity as a function of hepatocyte density appeared to be linear between 10,000-40,000 cells/well in 96-well plate format (FIG. 7)

Example 5

Effect of bile salts on transport of PC in hepatocytes: Hepatocytes at about 0.25 million cells/mL were incubated with 100 μg/mL d9-choline at various concentrations of taurocholic acid in Williams E buffer in the final volume of 100 μL at 37° C. under 5% $CO_2$ for 2 hours. Experiments were carried out in triplicate or duplicate. Suspensions were then centrifuged at 4000 RPM for 15 minutes at room temperature. The 4000 RPM supernatants were mixed with 3× volume isopropanol, and the mixtures were centrifuged at 4000 RPM for 20 minutes at 4° C. The supernatants were analyzed by LC/MS/MS for PC species.

Figure 8:
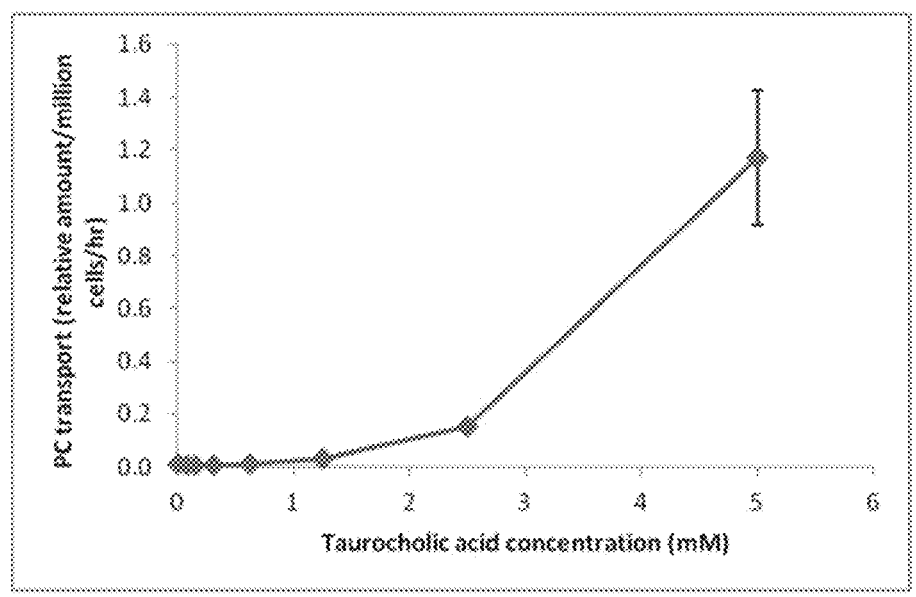
FIG. 8 displays the effect of taurocholic acid on the transport of phosphatidylcholine (PC, 34:2) in human hepatocytes, Human hepatocytes were incubated in Williams E buffer for 2 hours in the presence of d9-choline and taurocholic acid at various concentrations described in the methods. Cell-free mediums were mixed with isopropanol containing the analytical internal standard for LC/MS/MS analysis.

The activity of PC transport in hepatocytes was enhanced by bile salts in a concentration-dependent manner (FIG. 8).

Example 6

Effect of drug on the transport of bile salts in hepatocytes: Hepatocytes at about 0.25 million cells/mL were incubated with test drugs in the presence of 100 μg/mL d9-choline and 5 mM taurocholic acid in Williams E buffer in the final volume of 100 μL at 37° C. under 5% $CO_2$ for 2 hours. Experiments were carried out in triplicate or duplicate. Suspensions were then centrifuged at 4000 RPM for 15 minutes at room temperature. The 4000 RPM supernatants were mixed with 3× volume isopropanol and the mixtures were centrifuged at 4000 RPM for 20 minutes at 4° C. The supernatants were analyzed by LC/MS/MS for PC species.

Several drugs were tested for the potential modulation of the transport of PC in hepatocytes from mouse, rat, dog, monkey, and human. Some of the drugs tested are known to cause drug-induced liver injury (DILI) and/or cholestasis; some have no known association with DILI. The drugs tested include haloperidol, ketoconazole, saquinavir, chlorpromazine, imipramine, troglitazone, clotrimazole, griseofulvin, sulindac, biotin, furosemide, and penicillamine. The results are shown in Tables 2 and 3. The inhibition of PC transport in hepatocytes is correlated with the incidence of liver injury.

TABLE 2

Inhibition of PC export transportactivity by DILI drugs in human hepatocytes

| | 1 μM | 10 μM | 100 μM | Type |
|---|---|---|---|---|
| Biotin | A* | A | A | Non-DILI |
| Haoperidol | A | A | C# | DILI |
| Furosemide | A | A | A | Non-DILI |
| Ketoconazole | A | B^ | C | DILI |
| Saquinavir | A | B | C | DILI |
| Chlorpromazine | A | B | C | DILI |
| Imipramine | A | A | C | DILI |
| Penicillamine | A | A | A | Non-DILI |
| Troglitazone | A | B | C | DILI |

*A: ≤30%;
^B: 30-70%;
C: ≥70%.

TABLE 3

Inhibition (%) of PC export transport activity by DILI drugs in rat hepatocytes

| | 1 μM | 10 μM | 100 μM | Type |
|---|---|---|---|---|
| Biotin | A* | A | A | Non-DILI |
| Haloperidol | A | B^ | C# | DILI |
| Furosemide | A | A | A | Non-DILI |
| Ketoconazole | B | B | C | DILI |
| Saquinavir | A | C | C | DILI |
| Chlorpromazine | B | C | C | DILI |

TABLE 3-continued

Inhibition (%) of PC export transport activity by
DILI drugs in rat hepatocytes

| | 1 µM | 10 µM | 100 µM | Type |
|---|---|---|---|---|
| Clotrimazole | A | A | C | DILI |
| Griseofulvin | A | B | C | DILI |
| Imipramine | B | B | C | DILI |
| Sulindac | A | B | C | DILI |

*A: ≤30%;
~B: 30-70%;
C: ≥70%

I claim:

1. A composition for assessing a test agent's effect on phosphatidylcholine export transport and/or formation comprising a hepatocyte preparation, stable isotope- or radio-isotope-labeled choline compound(s), one or more bile salts, and one or more test agents.

2. The composition of claim 1 wherein the hepatocyte preparation comprises freshly prepared or cryopreserved hepatocytes.

3. The composition of claim 1 wherein the hepatocyte preparation comprises hepatocytes derived from human or animal liver tissues.

4. The composition of claim 3 wherein the hepatocytes are derived from human liver tissue.

5. The composition of claim 3 wherein the hepatocytes are derived from mouse, rat, dog, rabbit or monkey liver tissue.

6. The composition of claim 1 wherein the hepatocyte preparation comprises hepatocytes derived from stable cell lines.

7. The composition of claim 6 wherein the hepatocytes are derived from HepG2, Huh7, or HepaRG stable cell lines.

8. The composition of claim 1 wherein the hepatocyte preparation comprises hepatocyte cell lines expressing multidrug resistance protein 3 (MDR3).

9. The composition of claim 1 wherein the hepatocyte preparation is a pooled hepatocyte preparation.

10. The composition of claim 1 wherein the hepatocyte preparation is in the form of a suspension of hepatocytes.

11. The composition of claim 1 wherein the hepatocyte preparation is plated on a culture plate containing growth medium.

12. The composition of claim 1 wherein the concentration of hepatocytes in the hepatocyte preparation is between about 0.001 to about 1 million cells per milliliter.

13. The composition of claim 1 wherein the stable isotope- or radioisotope-labeled choline compound(s) include individually or in combination of deuterium- (1 to 13 deuterium atoms), tritium-, carbon-13 (1 to 5 carbon-13 atoms) and carbon-14 labeled choline.

14. The composition of claim 1 wherein the stable isotope-choline compound is d9-choline.

15. The composition of claim 1 wherein the test agent is a drug, drug candidate, biological, food component, herb or plant component, amino acid, peptide, protein, oligonucleotide, DNA or RNA.

16. The composition of claim 1 wherein the test agent is a drug or drug candidate.

17. The composition of claim 1, wherein the test agent's effect on phosphatidylcholine export transport and/or formation is used to assess potential treatments for hepatic cholestasis, potential for drug-drug interactions, and/or potential for drug-induced liver injury.

18. A drug discovery screen for determining the effect on phosphatidylcholine export transport and/or formation activity of multiple test agents comprising:
(a) selecting more than one test agent;
(b) for each test agent separately incubating a hepatocyte preparation and stable isotope- or radioisotope-labeled choline, bile salts, with or without a test agent at about 37° C. under conditions allowing phosphatidylcholine export transport and/or formation for a time sufficient to assess phosphatidylcholine export transport and/or formation stable isotope- or radioisotope-labeled choline derived phosphatidylcholine;
(c) for each test agent post-incubation separating extracellular media and intracellular media of the hepatocyte preparations; and
(d) for each test agent quantifying the stable isotope- or radioisotope-labeled choline derived phosphatidylcholine present in the extracellular and/or intracellular media of the post-incubation preparations;
(e) for each test agent determining the difference between the phosphatidylcholine export transport and/or formation activity without test agent and phosphatidylcholine export transport and/or formation activity with test agent.

19. The of drug discovery screen of claim 18 wherein the effect on phosphatidylcholine export transport and/or formation activity of the multiple test agents is reported in terms of percent inhibition.

20. The drug discovery screen of claim 18 wherein the effect on phosphatidylcholine export transport and/or formation activity of the multiple test agents is reported in terms of $IC_{50}$.

21. The drug discovery screen of claim 18 wherein the effect on phosphatidylcholine export transport and/or formation activity of the multiple test agents is reported in terms of Ki.

22. The drug discovery screen of claim 18 wherein the multiple test agents are ranked in terms of their effect on phosphatidylcholine export transport and/or formation activity.

23. The drug discovery screen of claim 18 wherein known inhibitors and non-inhibitors of phosphatidylcholine export transport activity are included in the incubation of step (b).

* * * * *